United States Patent [19]

Pott

[11] 4,015,463
[45] Apr. 5, 1977

[54] MEASURING DEVICE FOR THE WATER ACTIVITY OF FREE WATER CONTAINING VICTUALS

[75] Inventor: Otto Friedrich Pott, Mossingen, Germany

[73] Assignee: G. Lufft Metallbarometerfabrik, Stuttgart, Germany

[22] Filed: June 30, 1975

[21] Appl. No.: 592,062

[30] Foreign Application Priority Data
June 28, 1974 Germany .................................2431051

[52] U.S. Cl. .................................................. 73/73
[51] Int. Cl.² ........................................ G01N 33/00
[58] Field of Search ............................... 73/73–76, 73/335; 116/114 AM

[56] References Cited
UNITED STATES PATENTS

| | | | |
|---|---|---|---|
| 1,858,409 | 5/1932 | Mittelsteiner | 73/73 |
| 2,446,361 | 8/1948 | Clibbon | 73/73 |
| 2,611,481 | 9/1952 | Sargeant et al. | 73/73 |
| 2,929,241 | 3/1960 | Gebbart | 73/73 |
| 3,739,629 | 6/1973 | Cambell | 73/73 |
| 3,788,128 | 1/1974 | Strohecker | 73/73 |

FOREIGN PATENTS OR APPLICATIONS 22915 3/1968 Japan ................................... 73/76

*Primary Examiner*—Herbert Goldstein
*Attorney, Agent, or Firm*—Walter Becker

[57] ABSTRACT

A measuring apparatus for measuring the water activity of substances, especially victuals such as meat and meat products, containing free water, which has a lower section and an upper section detachably connected to the lower section. The lower section houses one or more measuring instruments comprising a container for receiving the sample of the victual to be checked. Mounted above the container is an instrument support supporting the instrument proper with corresponding pointer and scale observable through an observation opening in the upper section. The upper and lower sections preferably consist of foamed synthetic material, especially polystyrol hard foam.

13 Claims, 4 Drawing Figures

MEASURING DEVICE FOR THE WATER ACTIVITY OF FREE WATER CONTAINING VICTUALS

The present invention relates to a measuring device for the water activity of substances or materials, especially victuals, such as meat, food made of meat, etc., which contain water. A measuring device of the type involved comprises a box or container for receiving the sample of the respective victual and also comprises a carrier for the measuring gauge which is provided with at least one scale and can be introduced into said container. The measuring device serves for ascertaining the condition of the air which is enclosed in said container and surrounds the said sample while including a hydrometer and a thermometer.

The water activity briefly termed the $a_W$ value results from a substrate, for instance, with meat, from the number and the quantity of the ions and molecules therein and from the osmotic coefficient of the substance. Expressed in simplified terms, the water activity is that proportion of the water contained in a victual which is available for the increase of microorganisms. This proportion must not be considered the same as the chemically analytically determinable total water content. Only that portion of the total water content which is not bound by dissolved albuminous substance or protein, salts, sugar or in any other manner is available for the increase in the microorganisms.

Microorganisms, in other words, bacteria, yeasts, and molds, consist like most vegetable and animal cells of from 70 to 75% water and therefore, for their increase in a food substrate, for instance, in meat or goods of meat, require a sufficiently large quantity of not bound water.

For purposes of ascertaining the water activity, in other words of the $a_W$ values of meat and similar victuals, within the framework of the quality control within the plant and for official checking of foods there are available the above described measuring devices, the main components of which, comprise a container for receiving a sample of the respective victual and furthermore comprise an instrument carrier which can be placed in a sealing manner upon the container and which includes a hygrometer and a thermometer for ascertaining the condition of the air enclosed in the interior of said container. As soon as an equilibrium has been established between the activity of the sample and the relative temperature dependent air moisture of the air in the container, the $a_W$ value of the probe can be ascertained on the basis of the ascertained air moisture. The moisture indicated by the hydrometer will only then permit a sufficiently safe calculation of the water activity when the respective temperature in the interior of the container is measured and taken into consideration.

It is, therefore, an object of the present invention to keep the influence of the outer temperature of the surrounding air of the measuring device as low as possible over a longer period of time so that the hygrometer as well as the thermometer will have enough time to adapt themselves to the changes in temperature, and that these temperature changes will take place as slowly as possible within the interior of the container which contains the sample of the victual.

This object and other objects and advantages of the invention will appear more clearly from the following specification, in connection with the accompanying drawings, in which.

The measuring device according to the present invention is characterized primarily in that it includes a container of foamed synthetic material, especially of polystyrol hard foam material, which container is intended for receiving at least one measuring gauge, and is furthermore characterized in that said measuring device includes an observation opening for the scale of the measuring gauge carrier.

This arrangement will assure that the influences of temperature changes in the surrounding air of the measuring device can be kept rather low and that the hygrometer as well as the thermometer can assume a sufficiently parallel course of their temperature characteristic line.

The handling of the measuring device according to the invention is, in conformity with a further feature of the invention, considerably facilitated by the fact that the container is composed of two cup-shaped sections, namely, a bottom and a removable cover.

According to a preferred embodiment of the invention, the container has two recesses or cavities each being adapted to receive one of two measuring gauges and consequently, makes it possible in a particularly simple manner that one of the two measuring gauges can be gauged whereas the other measuring gauge is subject to a measuring operation for the water activity which requires a suitable time period.

In order to obviate the necessity that the measuring gauge for reading the indicated water activity has to be taken out of the container, the container may, according to a further development of the invention, comprise a clear sight disc which covers the observation opening and preferably airtight closes the same. This brings about the advantage that the measuring gauge will, during the measuring operation, remain thermally isolated relative to the surrounding air.

Figure 2:
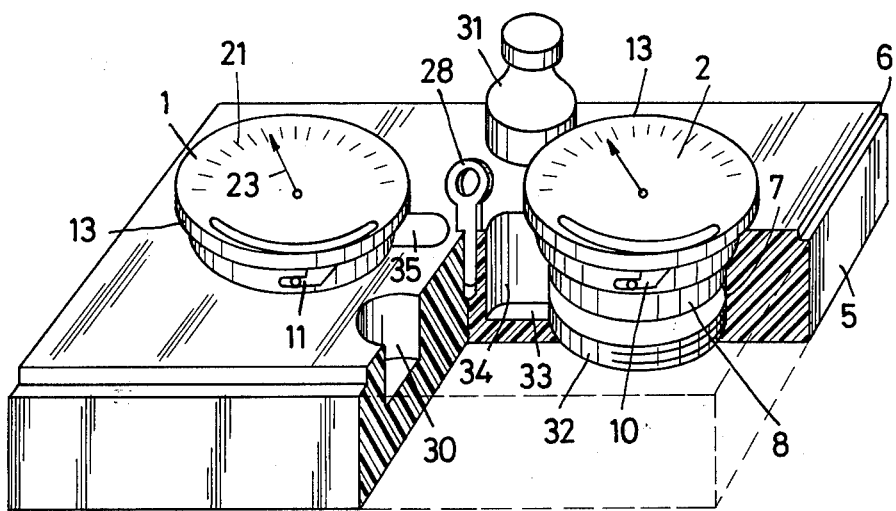
FIG. 2 illustrates the measuring device of FIG. 1, but with the cover removed, and represents a partial section taken along a right angle through the bottom part of the container.
Figure 3:
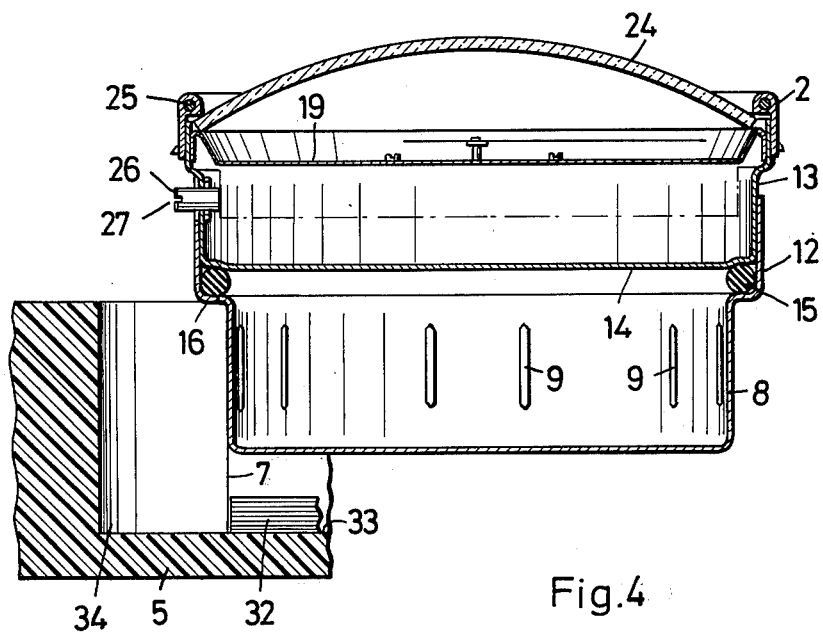
FIG. 3 shows an axial section through a measuring gauge forming a part of the above mentioned measuring device according to the invention.
Figure 4:
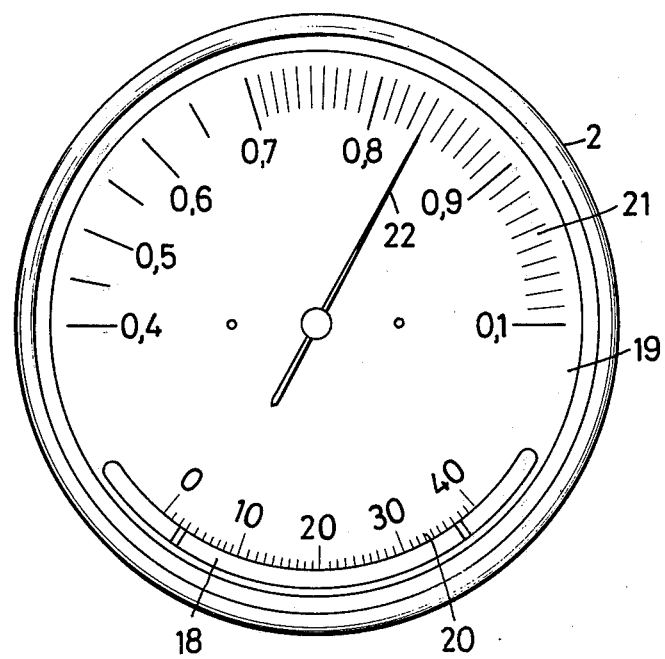
FIG. 4 is a top view of an $a_W$ value measuring gauge.

Referring now to the drawings in detail, the illustrated measuring device, as mentioned above, serves for ascertaining the water activity of meat and goods of meat, and other victuals, subject to a relatively fast spoilage. The illustrated measuring device comprises two measuring gauges 1 and 2 which are exchangeable with regard to each other. One of these measuring gauges 1 and 2 is illustrated in FIGS. 3 and 4 and both correspond to each other fully in operation as well as in construction. For purposes of mounting these two measuring gauges, the measuring device comprises a container 3 which is made of a hard foam synthetic material, namely, of foam polystyrol. The container comprises an upper section or cover 4 and a bottom section 5 which includes a formed-on groove or notch 6 for placing the cover 4 on the container 3. For purposes of mounting the two measuring gauges 1 and 2, the bottom section 5 is provided with two recesses 7 of which FIG. 2 shows only one.

The two measuring gauges 1 and 2 respectively are supported in a tightly closed receptacle which includes a bottom part or a deep drawn container 8 of rust-proof steel, into which the samples of the victuals to be checked can be inserted. The recesses 7 are as to their diameter dimensioned so close that the containers with their longitudinal ribs 9 projecting on the container mantle toward the outside will find a rotation-resistant hold in said bores and can be connected with the top part or gauge carrier 13 of one of the two gauges by means of a bayonet joint 10, 11 which is arranged in the marginal section of the container widening to a collar 12. In order to assure a sufficient seal of the inner space of the container 8 which receives the sample of the victual, the bottom 14 is, by means of a circular O-ring 15, clamped against the annular shoulder 16 which ring is arranged between the collar 12 and the mantle surface of the container 8. The bottom 14 is provided with a number of openings (not shown in the drawings) for the passage of the inner air of container 8, which air is to be measured as to its humidity content.

The gauge carrier 13 comprises a standard hygrometer, for instance, with a thread, band, hair, spiral, or similar measuring element, not shown in the drawings. The gauge carrier 13 furthermore comprises a bent mercury thermometer 18 which is coaxially arranged with regard to the longitudinal axis of the gauge carrier 13. A temperature scale 20 associated with the thermometer 18 is arranged on a scale disc 19 which closes the carrier 13 off at its upper end. An $a_W$ scale 21 extends over the other section of the scale disc 19 while above the scale 21 there is rotatably arranged a pointer 22, 23 for indicating the respective humidity value $a_W$. Above the scale disc 19 there is provided in a known manner an arched clear sight disc 24 which is secured in its position by means of a marginal ring 25 sprung thereupon. The ring 25 is, similar to the housing of the gauge carrier 13, made of rust resisting steel and therefore does not require any service for keeping the same clean.

Figure 1:
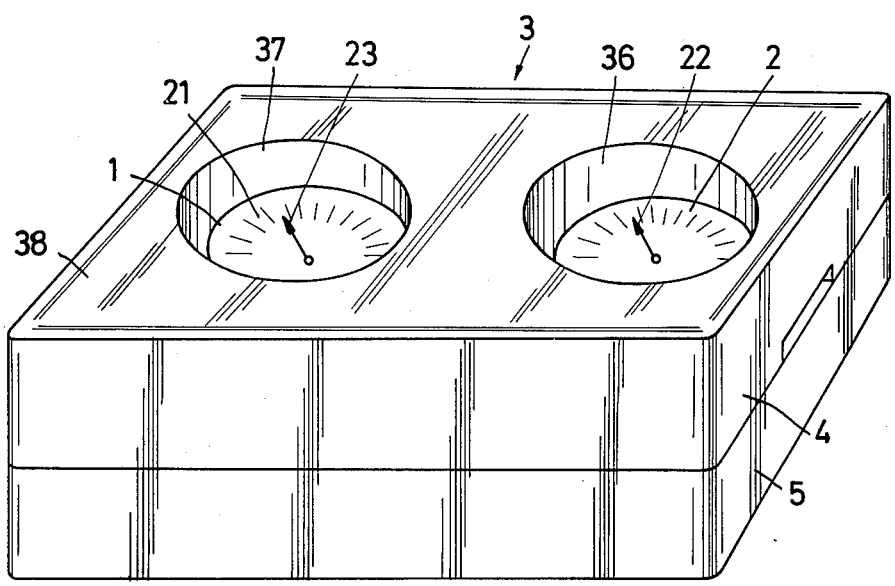
FIG. 1 illustrates an isometric view of a measuring device according to the invention with its container of insulating material.

With the illustrated embodiment, the carrier 13 has a radially outwardly protruding adjustable shaft 26 which at its end face is provided with a transverse slot 27 for engagement with a screw driver 28. In order to have a screw driver handy all the time, the bottom section is provided with a cut, not designated in the drawings, into which the screw driver 28 can be inserted, as shown in FIG. 2. As will be evident from FIG. 2, in the bottom section 5, there are provided two cylindrical recesses which are arranged on both sides of the screw driver 28 and in which in FIG. 1 only one recess 30 is shown. These recesses serve for respectively receiving two bottles 31 in which a gauging liquid can be kept of a saturated barium-chloride solution. A hygroscopic insertable sheet 32 is permeated with said gauging liquid. These insertable sheets or foils are stacked in a stack at the bottom 33 of the recess 7 intended for receiving the containers 8. In order to be able easily to grasp one of the foils kept in supply and to withdraw it from the recess 7, the two recesses 7 continue toward the inserted screw driver 28 in the form of two thumb cuts 34 and 35, as shown in FIG. 2.

Inasmuch as the equilization of the moisture of the air in the container with the air in the carrier 13, which humidity determines the indicated measuring value requires a longer period of time, it is frequently desired to carry out a plurality of readings in a minimum of time intervals. In order to make sure that to this end the measuring gauges need not be withdrawn from the container, the cover 4 has above the scale disc 19 of the two measuring gauges 1 and 2, two circular observation windows 36 and 37 which taper conically toward said scale discs. Both observation windows are, by means of a continuous clear sight disc closed in an airtight manner to such an extent that the measuring results are, for all practical purposes, not influenced by changes in the temperature.

The design of the container 3 according to the present invention and the measuring gauges arranged therein permit a simple ascertainment of the moisture content which is indicated by means of the two pointers 22 and 23 and can be read on the scale 21 extending over an angle of 180°. During the temperature measurement which is necessary for a possible correction of the indicated $a_W$ values, no disturbances can occur because the capillary thermometer 18 is closed completely and contains a colored red column. Also, when using the device according to the invention over a longer period of time there will exist no corrosion danger because the housing of the carrier 13 as well as of the containers 8 serving as measuring engaging containers consist of rust resistant steel. When gauging the measuring gauges, no difficulties are encountered because the gauging liquid can always be kept handy in a sufficient quantity in the two bottles 31, and the adjusting shaft 26 is easily accessible. The gauging liquid itself will suffice for a great number of operations because only one of the insert foils 23 on the stack has to be withdrawn and is humidified for engaging purposes. Inasmuch as always two complete measuring gauges are held ready in the container in the form of a set in which one set may be used alternately for gauging while the other set is used for measuring, the device is continuously ready for operation. When measuring and gauging, the measuring gauges remain in the container 3. They can be read through the clear sight disc 38 in a proper manner. Inasmuch as temperature changes are during the measurement and the gauging kept away from the device according to the invention, a high measuring precision may be assured.

It is, or course, to be understood that the present invention is, by no means, limited to the specific showing in the drawings, but also comprises any modifications within the scope of the appended claims.

What I claim is:

1. A readily portable measuring apparatus for measuring the water activity of substances containing free water, including a foamed lower section of insulating material, a foamed upper section of insulating material connected to said lower section, a closed receptacle formed of separable top and bottom parts, said bottom part receiving the substance to be measured, the top part carrying hygrometer means and thermometer means therein, the bottom part of said receptacle frictionally engaging in a recess in said lower section, said top and bottom parts being separably connected with sealing means therebetween to form the closed receptacle, said top part opening to said bottom part, said top part projecting above said lower section, said upper section being recessed to surround and extend above said top part, the instruments in said top part being readable from above said receptacle and said upper section having an opening through which said instruments may be observed.

2. An apparatus in combination to claim 1, in which said measuring gauge means includes two interchangeable measuring gauges.

3. An apparatus in combination according to claim 2, in which both said upper and lower sections are of polystyrol hard foam.

4. An apparatus in combination according to claim 3, in which said lower section is provided with recess means for receiving said container means and said supporting means with close lateral tolerance.

5. An apparatus in combination according to claim 4, in which said upper section is detachably connected to said lower section.

6. An apparatus in combination according to claim 5, in which the measuring gauge means includes at least two measuring gauges, and in which said lower section comprises identical recess means corresponding in number to said measuring gauges for receiving the same.

7. An apparatus in combination according to claim 6, in which the depth of said recess means is such as to leave space at the bottom of said recess means for a stack of gauging insert foils.

8. An apparatus in combination to claim 2, in which the walls of said receptacle are circular and made of rust-proof steel.

9. An apparatus in combination according to claim 1, which includes adjusting means connected to said hygrometer means and extending through the outer wall of said upper section for adjusting said hygrometer means, and elastic sealing meand completely sealing said adjusting means relative to the interior of said upper section.

10. An apparatus in combination according to claim 9, which includes calibration tool means detachably arranged in said lower section for adjusting said adjusting means.

11. An apparatus in combination to claim 10, in which said thermometer means includes a curved thermometer substantially coaxially arranged with regard to the axis of said upper section and observable by said means for permitting observation of said scales and pointers.

12. An apparatus as claimed in claim 1, in which said opening in the upper section is closed by a transparent member.

13. An apparatus as claimed in claim 12, which includes sealing means between said transparent member and said upper section.

* * * * *